United States Patent [19]

Meldahl

[11] 4,232,675

[45] Nov. 11, 1980

[54] MALE CONTRACEPTIVE ARRANGEMENT

[76] Inventor: Edward N. Meldahl, 230 W. 55th St., Apt. 11D, New York, N.Y. 10019

[21] Appl. No.: 24,782

[22] Filed: Mar. 29, 1979

[51] Int. Cl.$^3$ ............................................... A61F 5/42
[52] U.S. Cl. ..................................... 128/294; 128/79
[58] Field of Search ................... 128/132 R, 294, 295, 128/79

[56] References Cited

U.S. PATENT DOCUMENTS

| | | | |
|---|---|---|---|
| 967,269 | 8/1910 | Tibbs | 128/294 |
| 2,410,460 | 11/1946 | Robinson | 128/294 |
| 2,433,538 | 12/1947 | Warner | 128/294 |
| 3,648,700 | 3/1972 | Warner | 128/294 |

FOREIGN PATENT DOCUMENTS

| | | | |
|---|---|---|---|
| 211350 | 6/1909 | Fed. Rep. of Germany | 128/294 |
| 2020280 | 11/1971 | Fed. Rep. of Germany | 128/294 |
| 946822 | 12/1948 | France | 128/294 |

*Primary Examiner*—Lawrence W. Trapp
*Attorney, Agent, or Firm*—Warren D. Flackbert

[57] ABSTRACT

A male contraceptive arrangement defined, basically, by a modified condom, i.e. one having a shorter length than now commercially available and a configuration particularly adapted to contain semen; a spermicidal ring received within the condom; and, an elasticized retaining cover adapted to position the condom on the male organ.

In one invention form, a harness, disposed on the glans penis, extends to the spermicidal ring, where, in another invention form, the harness includes sensitivity segments which are located rearwardly of the glans penis. In a further invention form, additional positive positioning of the condom is afforded through an elasticized retaining device arranged over the condom at a position in front of the spermicidal ring and to the rear of the elasticized retaining cover.

The invention also presents a wrap-around positioning device, used in association with the rim or beaded end at the opening to the condom, which serves to further assure placement of the contraceptive arrangement during use.

14 Claims, 10 Drawing Figures

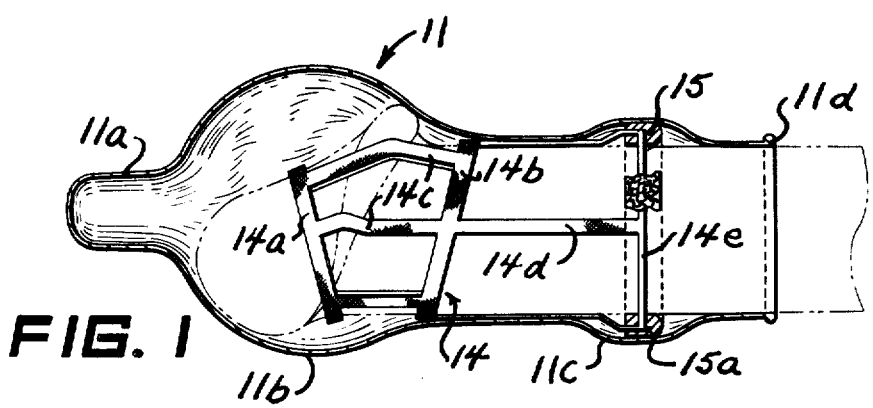
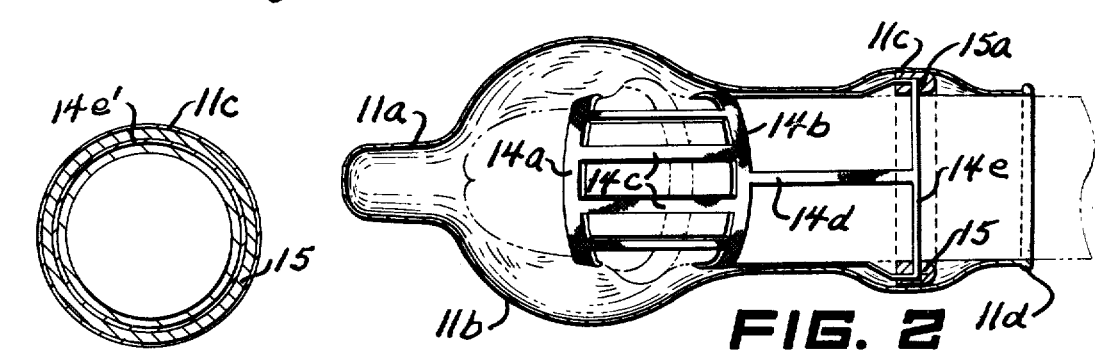
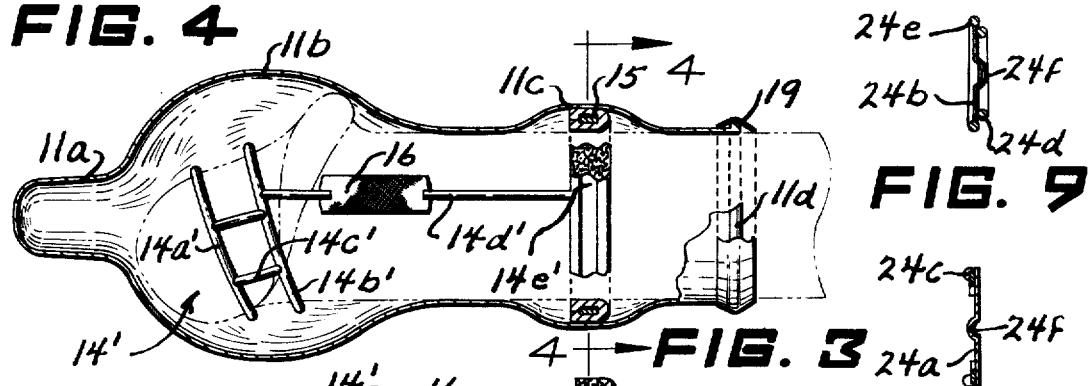
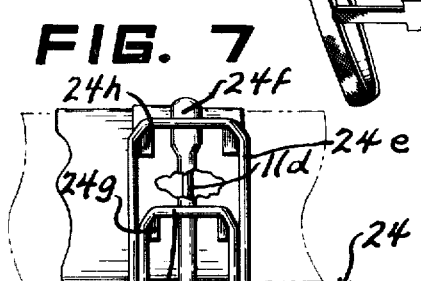
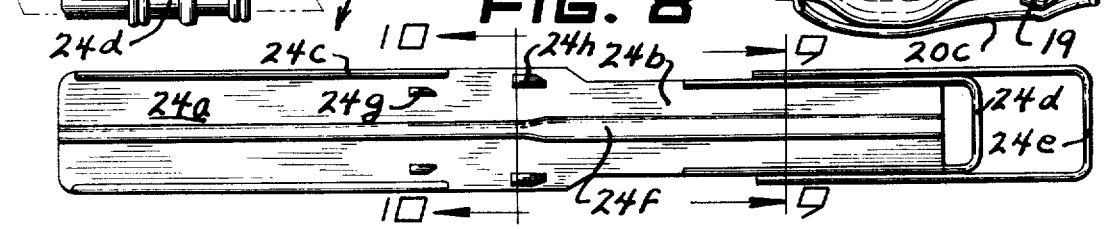

MALE CONTRACEPTIVE ARRANGEMENT

As is known, a serious overpopulation problem is threatening many areas of the world and, accordingly, an important need arises for effective and yet convenient birth control. While existing contraceptive approaches need not be discussed in detail herein, the known male condom has been recognized as a relatively reliable and one of the safest contraceptives in use. One advantage of such condom is that it does not normally occasion any side effects either to the male or female. On the other hand, drawbacks to the present male condom are the loss of sensitivity during sexual performance and the fact that the condom must be removed from the vagina shortly following ejaculation so as to prevent leakage of semen into the vagina.

The invention provides an improved male contraceptive arrangement, overcoming the aforestated objections to the male condom currently in use. Broadly, the contraceptive arrangement includes a modified condom, both as to overall length and plan configuration; a ring for receiving or incorporating a spermicide, where the latter is positioned around the male organ and beneath an enlargement near the open or entry end of the modified condom; and, an elasticized cover which extends over the rim or beaded end of the condom and serves as one approach for retaining the condom on the male organ.

In a preferred embodiment, a harness, disposed within the condom and about the glans penis, extends to the spermicidal ring, where, in a modification to the preferred embodiment, the harness includes the use of sensitivity segments, typically positioned by elasticized bands or threads, for example, which extend in the space behind the glans penis and towards the spermicidal ring. The sensitivity segments may be in the form of a textured, velvet, or like strip material affording stimulation of the male organ, and the spermicidal ring is typically made from cellulose or other material suitable for receiving and containing a spermicide.

In another invention form, and usable either with or without the aforedescribed harness and/or the retaining cover, an elasticized retaining device is presented for even more positively positioning the condom arrangement during use. In this connection, the elasticized retaining device extends over the rear portion of the condom, and, more specifically, over the concealed spermicidal ring and over the aforementioned elasticized retaining cover. Such a retaining device serves a further purpose of preventing, or at least blocking or limiting, the unwanted travel of semen towards the entry or rear end of the condom.

An alternative condom positioning approach presented by the invention is defined as an elasticized tie-in or wrap-around device located at the rim or beaded end of the condom, the elasticity permitting accommodation for tumescence or detumescence of the male organ.

The invention also suggests, if desired, for the use of an independent sensitivity member, typically disposed on a member encircling the male organ in a region somewhat behind the discussed contraceptive arrangement. In this connection, the sensitivity member may assume any plan configuration and serves added stimulation during sexual performance.

In any event, and as will become further evident from the following description, the invention affords an important contribution to the area of male contraception, and reference is now made to the accompanying drawing, wherein FIG. 1 is a view in side elevation, partly in vertical section, showing a male contraceptive arrangement, including a harness, in accordance with the teachings of the invention, where a male organ is shown in phantom;

FIG. 2 is a top plan view of the contraceptive arrangement of FIG. 1, showing other details thereof;

FIG. 3 is a view in side elevation, showing a modified form of the invention, including the usage of a harness which in this instance has sensitivity segments, and, the usage of an elasticized retaining cover;

FIG. 4 is a view in vertical section of the spermicidal ring of FIG. 3, taken at line 4—4 of such figure and looking in the direction of the arrows;

FIG. 5 is a view in side elevation of a modified form of harness, including sensitivity segments, comparable to the usage shown in FIG. 3;

FIG. 6 is a view in elevation of an auxiliary elasticized retaining device;

FIG. 7 is a top plan view of a wrap-around or tie-in positioning device forming part of the invention, showing such in use in combination with the condom of the preceding figures;

FIG. 8 is also a top plan view of the positioning device of FIG. 7, but in an unwrapped condition, i.e. as such appears prior to placement for usage;

FIG. 9 is a view in section, taken at line 9—9 on FIG. 8 and looking in the direction of the arrows, showing certain details of the wrap-around positioning device of FIGS. 7 and 8; and, FIG. 10 is another view in section, in this instance, however, taken at line 10—10 on FIG. 8 and looking in the direction of the arrows, showing still further details of the wrap-around positioning device of FIGS. 7 and 8.

For the purposes of promoting an understanding of the principles of the invention, reference will now be made of the embodiments illustrated in the drawing and specific language will be used to describe the same. It will nevertheless be understood that no limitation of the scope of the invention is thereby intended, such alterations and further modifications of the illustrated devices and such further applications of the principles of the invention as illustrated therein being contemplated as would normally occur to one skilled in the art to which the invention relates.

Referring now to FIGS. 1 and 2, one form of contraceptive arrangement of the invention includes a condom 11 having a closed front end in the form of a reservoir or nipple 11a, a bell-shaped portion 11b, and an enlargement 11c disposed between bell-shaped portion 11b and a rim or projecting bead 11d surrounding the entry or open rear end. The appearance of the condom 11 is the subject of co-pending United States design patent application Ser. No. 862,354, filed Dec. 20, 1977, and entitled MALE CONTRACEPTIVE, where the inventorship is the same. As an aid to understanding, a male organ is representatively shown in phantom in the figures, where applicable.

As further evident in FIGS. 1 and 2, the arrangement of the invention includes an assembly defined by a harness 14 represented as rings 14a and 14b secured together by connecting members 14c, positioned around and, also, rearwardly of the glans penis, and a spermicidal ring 15 concealed beneath the enlargement 11c of the condom 11. Integral bands 14d extend between the front part of the harness 14, i.e. that surrounding the glans penis, and a rear ring 14e inserted within a forwardly disposed slit 15a in the spermicidal ring 15. The rings 14a, 14b and 14e, connecting members 14c, and bands 14d, are typically made from resilient material, such as rubber.

As to the spermicidal ring 15, such is, as stated, slitted, at 15a, in a forward direction, i.e. toward the head of the male organ, and is made from cellulose or other material suitable for receiving and containing a spermicide preparation, such as Ricinoleic acid 0.78, p-diisobutylphenoxpolyethoxyethanol 1.00% and boric acid 3.00%. As should be understood, spermicide is introduced into ring 15 prior to usage of the contraceptive.

With reference now to FIGS. 3, 4 and 5, a modified contraceptive arrangement is shown which is generally similar to that of FIGS. 1 and 2. The changes lie primarily in harness 14' and the use of an auxiliary elasticized retaining cover 19.

As to the former, the basic difference is in added sensitivity segments 16 which are disposed at the mid to front portion of bands 14d' extending between the front of the harness 14' and the spermicidal ring 15. In this connection, the harness 14' also includes a rear ring 14e' as in the invention embodiment of FIGS. 1 and 2. In any event, one or more of such sensitivity segments 16 can be employed, each typically made from velvet, silk or even a textured rubber material. In some arrangements, the bands 14d' can be elasticized string or thread. FIG. 5 further shows a form wherein the front of the harness 14' is a loop 14f which encircles the glans penis. It should be understood that the sensitivity segments 16 serve for added sexual stimulation during usage.

As to the other presented change, and looking now at the entry or open rear end of the condom 11, an elasticized retaining cover 19 is disposed over the rim or projecting head 11d thereof, such being typically made from a resilient material, as rubber, and serving to position the condom 11 on the male organ. Additionally, the resiliency of the elasticized retaining cover 19 further serves as a barrier to unwanted flow of semen from the condom 11. As evident, the cover 19 may also be used in combination with the contraceptive arrangement of FIGS. 1 and 2.

In the invention embodiment of FIG. 6, a further retaining device 20 is disclosed which may be used with the assembled harness 14–14' and spermicidal ring 15 described in connection with FIGS. 1 to 5, inclusive. More specifically, the retaining device 20 is defined by rings 20a and 20b, connected together by members 20c, each preferably made from resilient material, such as rubber. Typically, ring 20a is disposed over the condom 11 in front of the enlargement 11c for the spermicidal ring 15. The ring 20b is positioned behind the rim or bead 11d and elasticized retaining cover 19 described in the FIG. 3 embodiment. In other words, the retaining device 20 further assures positive placement of the contraceptive during use and serves, additionally, to occlude semen movement from the condom 11.

FIGS. 7, 8, 9 and 10 are directed to a tie-in or wrap-around positioning device 24 which serves a still further alternative approach for retaining the contraceptive arrangements described above in placement during usage. As should be apparent in FIG. 7, the positioning device 24 cooperates, in a wrapped relationship, with the bead or rim 11d at the open end of the condom 11, serving positive securing purposes and the prevention of unwanted semen flow. A further contraceptive effect results with the use of a spermicide preparation on the device prior to wrapping for placement.

In any event, and looking at FIG. 8, the positioning device 24 is shown in an unrolled condition, i.e. prior to placement around the condom 11 on the male organ. Positioning device 24 includes an elongated body member, preferably made from rubber for stretching reasons, having a wide portion 24a and a reduced portion 24b; ridges 24c along the edges of the wide portion 24a; elastic members 24d and 24e extending from the free end of the reduced portion 24b; a longitudinal centrally disposed groove or channel 24f, one end of which is adapted to be wrapped over the opposite end because of width considerations (see FIGS. 7, 9 and 10); and, hooks 24g and 24h, in pairs, for receiving the ends of the elastic members 24d and 24e when arranged for use.

In use, and noting first the embodiment of FIGS. 1 and 2, the harness 14 and the spermicidal ring 15 are located in the illustrated position on the male organ, i.e. the front end of the harness 14 surrounds the glans penis, where the rear end thereof (ring 14e) extends into the slit 15a in the spermicidal ring 15. The condom 11 is then drawn over the preceding, where the enlargement 11c on the condom 11 overlies the spermicidal ring 15.

In the embodiment of FIGS. 3 to 5, inclusive, which includes the sensitivity segments 16, a similar assembled relationship is achieved, where it should again be noted that the sensitivity segments 16, extending between the harness 14' and the spermicidal ring 15, serve a stimulating effect which would not be normally achieved with the use of a conventional condom. In any event, in this instance the elasticized retaining cover 19 is employed, where such is placed over the rear rim or bead 11d of the condom 11 for securing and semen blocking purposes. The harness 14' may assume the representatively illustrated forms of FIGS. 3 and 5.

In the event that alternative condom retaining is desired, the retaining device 20 of FIG. 6 may be employed. In this connection, the spaced-apart rings 20a and 20b are positioned as illustrated in such figure, i.e. respectively in front of the enlargement 11c on the condom 11 and to the rear of the elasticized retaining cover 19. As mentioned, in addition to securing, even more positive semen containment is another end result.

FIGS. 7 to 10, inclusive, show still an additional positioning device 24, in this instance affording a wrapped relationship with the rear rim or bead 11d of the condom 11. Importance lies in the ready accommodation of the device 24 to the circumference of the penis, either at a state of tumescence or detumescence, due to the "stretch" factor of the utilized material. As stated, a spermicide preparation can also be used in the channel or groove 24f prior to rolling on the male organ for placement.

Accordingly, and in view of the preceding, the invention affords a positive approach to birth control through the prevention of a unique male contraceptive arrangement in various adaptations. The contraceptive of the invention is easily and positively positioned for use, and, further, affords sensitivity not available heretofore with conventional type condoms. Additionally, the condom presented herein is considerably shorter in length than the ordinary condom, typically being approximately 10.5–11.5 centimeters, and wider, approximately 5.0 centimeters, measured flat, around the glans penis, meaning more sensitivity for sexual performance. Moreover, and as indicated, the spermicidal ring 15 is susceptible for use with various commercially available spermicidal jellies or preparations.

The described male contraceptive arrangement is susceptible to various changes within the spirit of the invention, as, for example, the number of sensitivity segments 16 employed; the particular harness 14—14' arrangement; the manner of spermicide material retention in the ring 15; still other types of auxiliary retaining means; and, the like. While not detailed herein, the invention further encompasses the use of a separate stimulating arrangement positioned apart or independently from the described contraceptive approaches, i.e. rearwardly of the latter on the male organ. In summary, therefore, the preceding should be considered illustrative and not as limiting the scope of the following claims:

I claim:

1. A male contraceptive arrangement received by a penis comprising a condom having a rim surrounding an entry end and an enlargement proximate said entry end, a resilient retaining cover overlying said rim, and a spermicide receiving member disposed within said condom beneath said enlargement serving both operative spermicidal extruding and positioning purposes.

2. The male contraceptive arrangement of claim 1 where said condom has a closed end opposite said entry end and where a bulged portion in a loosely fitting relationship with the glans of said penis exists between said enlargement and said closed end.

3. The male contraceptive arrangement of claim 2 where a penis supported harness assembly is disposed within said condom at said bulged portion and extends to said spermicide receiving member.

4. The male contraceptive arrangement of claim 3 where said penis supported harness assembly encircles a portion of the glans of said penis.

5. The male contraceptive arrangement of claim 2 where said penis supported harness assembly is disposed within said condom at said bulged portion, and where a textured segment is positioned by said penis supported harness assembly and lies between said bulged portion of said condom and said spermicide receiving member.

6. The male contraceptive arrangement of claim 4 where said textured segment is located by elastic members.

7. The male contraceptive arrangement of claim 2 where said closed end of said condom defines a nipple.

8. A male contraceptive arrangement comprising a condom having a rim surrounding an entry end and an enlargement proximate said entry end, a resilient retaining cover overlying said rim, a spermicide receiving member disposed within said condom beneath said enlargement, and a retaining device overlying said enlargement and said resilient retaining cover and extending in a direction toward the end of said condom opposite said entry end and in an opposite direction beyond said resilient retaining cover disposed on said rim of said entry end.

9. The male contraceptive arrangement of claim 2 where said bulged portion of said condom has a bell shape.

10. The male contraceptive arrangement of claim 1 where said spermicide receiving member is a cellulose ring.

11. A male contraceptive arrangement comprising a condom having a rim surrounding an entry end and an enlargement proximate said entry end, a resilient retaining cover overlying said rim, a spermicide receiving member disposed within said condom beneath said enlargement, and a positioning device encircling said condom in a wrapped relationship.

12. The male contraceptive arrangement of claim 11 where said positioning device cooperates with said rim surrounding the entry to said condom.

13. The male contraceptive arrangement of claim 12 where said positioning device includes a raised longitudinal groove which cooperates with said rim.

14. The male contraceptive arrangement of claim 11 where said positioning device, when unrolled, is defined by an elongated body including latching means adapted to be selectively engaged by an elastic tying member when in a rolled condition.

* * * * *